(12) United States Patent
Ellman et al.

(10) Patent No.: US 6,432,105 B1
(45) Date of Patent: Aug. 13, 2002

(54) BIPOLAR ELECTROSURGICAL HANDPIECE FOR TREATING TISSUE

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/728,382

(22) Filed: Dec. 4, 2000

(51) Int. Cl.[7] ............................................. A61B 18/18
(52) U.S. Cl. ............................ 606/48; 606/41; 606/50
(58) Field of Search ............................. 606/41, 45, 46, 606/47, 48, 49, 50; 607/96, 98, 101, 104, 105

(56) References Cited

U.S. PATENT DOCUMENTS 5,007,908 A * 4/1991 Rydell ........................... 606/47
6,210,405 B1 * 4/2001 Goble et al. ................... 604/35

* cited by examiner

*Primary Examiner*—Rosiland S. Kearney

(57) ABSTRACT

A bipolar electrosurgical instrument that is configured for use in MIS and other electrosurgical procedures. The instrument is constructed with a rigid end as a bipolar electrode comprising spaced rounded electrodes. The electrode preferably comprises spaced hemispherically-shaped electrically conductive members projecting from the end of the housing. When energized, a bipolar discharge is generated between the bare ends of the electrode.

7 Claims, 3 Drawing Sheets

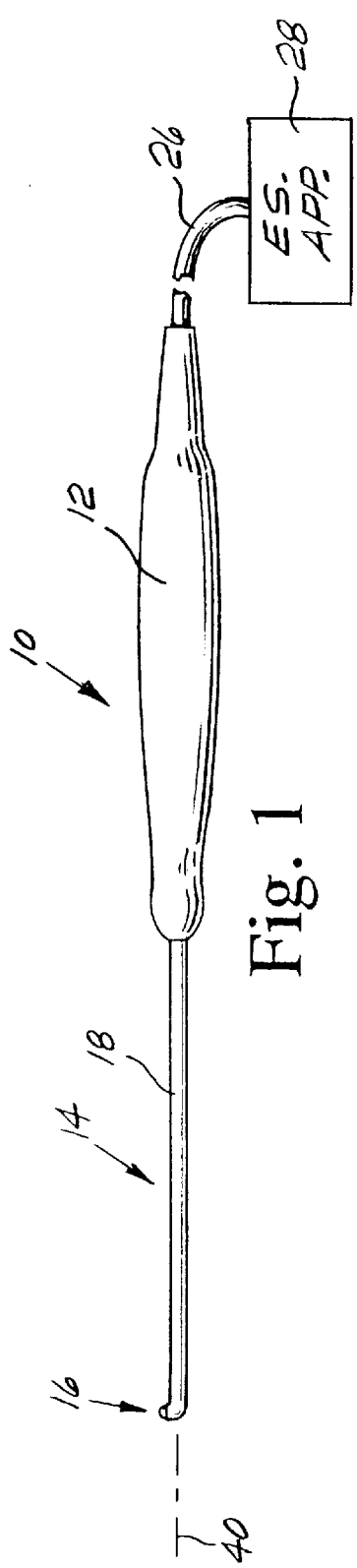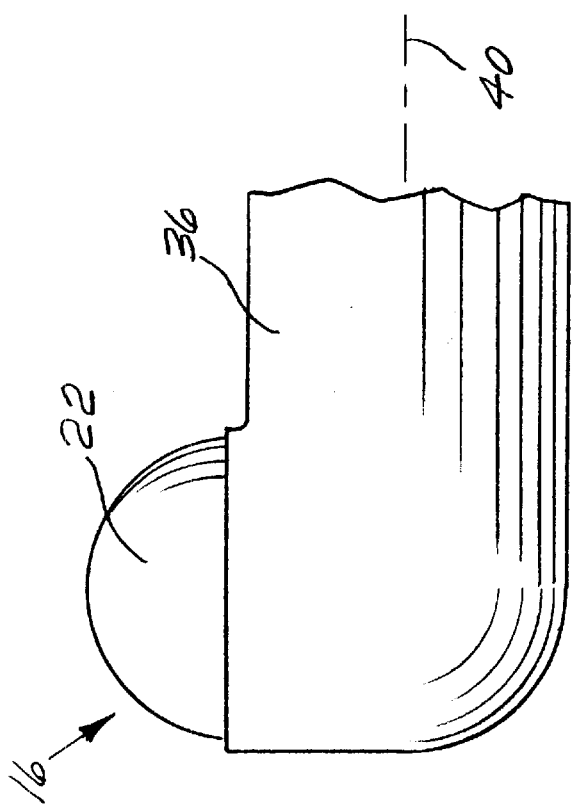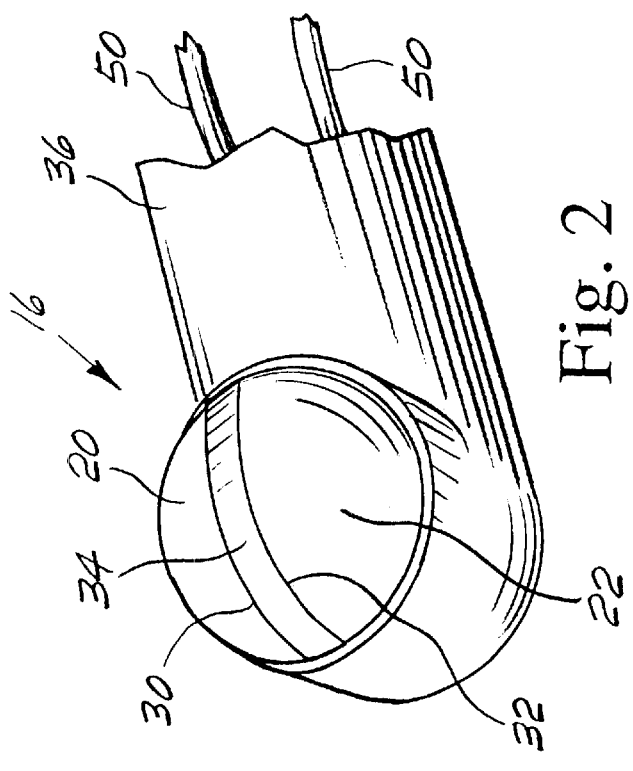

BIPOLAR ELECTROSURGICAL HANDPIECE FOR TREATING TISSUE

RELATED APPLICATION

U.S. application, Ser. No. 09/303,839, filed May 3, 1999, commonly owned, for "Electrosurgical Handpiece For Treating Tissue", of which the present application is a continuation-in-part.

U.S. application, Ser. No. 09/393,286, filed sEP. 10, 1999, commonly owned, for "Electrosurgical Handpiece For Treating Tissue", of which the present application is a continuation-in-part.

U.S. application, Ser. No. 09/425,313, filed Oct. 25, 1999, commonly owned, for "Electrosurgical Handpiece For Treating Tissue", of which the present application is a continuation-in-part.

U.S. application, Ser. No. 09/483,994, filed Jan. 18, 2000, commonly owned, for "Electrosurgical Handpiece For Treating Tissue", of which the present application is a continuation-in-part.

This invention relates to a bipolar electrosurgical handpiece and an activator for an electrosurgical handpiece.

BACKGROUND OF THE INVENTION

Our prior application, Ser. No. 09/303,839, describes a novel electrosurgical handpiece for treating tissue in a surgical procedure commonly known as minimally invasive surgery (MIS). Among the features described and claimed in the prior application is an electrosurgical handpiece that can be used in MIS and reduces the danger of excessive heat causing possible patient harm. This is achieved in one embodiment by an electrosurgical handpiece that is bipolar in operation and that is configured for use in MIS. The bipolar operation confines the electrosurgical currents to a small active region between the active ends of the bipolar electrode and thus reduces the possibility that excessive heat will be developed that can damage patient tissue. Moreover, the position of the active region can be controlled to avoid patient tissue that may be more sensitive to excessive heat. Preferably, the handpiece is provided with a dual compartment insulated elongated tube, each of the compartments serving to house one of the two wires of the bipolar electrodes. The electrode for MIS use is preferably constructed with a flexible end controllable by the surgeon so as to allow the surgeon to manipulate the end as desired during the surgical procedure. In a preferred embodiment, the flexible end is achieved by weakening at the end the housing for the electrode, and providing a pull string or wire connected to the weakened housing end and with a mechanism at the opposite end for the surgeon to pull the string or wire to flex the housing end to the desired position. This feature allows the surgeon to position the active electrode end at the optimum location for treating, say, a herniated disk to remove undesired regions and to provide controlled heat to shrink the tissue during surgery. In FIGS. 3–7 of the prior application, a suitable bipolar electrode is described, which comprises a pair of rounded electrodes with spaced flat sides separated by an insulating layer. FIGS. 8–10 illustrate a suitable unipolar electrode construction of the flexible end handpiece. FIG. 12 illustrates how such an electrode can be used for the reduction of herniated disks in a laparoscopic procedure. FIG. 20 shows a scissors end that can be constructed as a bipolar electrode for certain purposes.

Our prior application, Ser. No. 09/393,286, describes a modified bipolar electrode construction using the flexible end handpiece, the modified bipolar electrode having spaced prongs.

Our prior application, Ser. No. 09/425,313, describes a modified bipolar electrode configured to provide easier flexing of the handpiece end, or more controlled flexing and positioning of the handpiece end.

Our prior application, Ser. No. 09/483,994, describes a modified bipolar electrode construction using the flexible end handpiece, the modified bipolar electrode having spaced loops.

There is a need in the art for rigid electrodes, i.e., without a flexible end, for treating orthopedic ailments, such as joint ailments of the shoulder and knee, especially in an minimally invasive surgery (MIS) environment, also referred to from time to time as arthroscopy.

SUMMARY OF THE INVENTION

The present invention is a continuation-in-part of the four prior applications and hereby incorporates by reference the total contents of the four prior applications, Ser. Nos. 09/303,839, 09/393,286, 09/425,313, and 09/483 994. The present invention describes and claims among other things a bipolar electrode comprising spaced rounded electrodes with a rigid non-flexible end. Since the present application otherwise makes use of the same teachings of the prior applications, it was felt unnecessary to repeat in the body of this specification many of the details present in the contents of the prior application. The present description will be confined solely to the modifications in the handpiece or electrode which will still achieve the same benefits as with the constructions of the prior applications. For more details, the reader is directed to the prior applications.

The new handpiece end constructions of the present improvement uses the bipolar principle and are configured to provide more controlled distribution of the electrosurgical currents to the tissue to be modulated.

In a preferred embodiment, the electrode ends are formed by dual projecting, spaced, rounded electrodes, preferably configured as hemispherical or flattened hemispherical electrodes each connected to a terminal of the bipolar source. In a first preferred embodiment, the hemispherical electrodes project laterally in spaced parallel planes approximately the same distance from the insulated end of the electrode mounted in a rigid handpiece. In a second preferred embodiment, the electrodes are substantially hemispherical in configuration, by which is meant that the electrodes are more elliptically shaped with one axis longer than the transverse axis. By "laterally" is meant that the hemispherical electrodes extend at right angles or at an acute angle, such as 45°, with respect to the longitudinal axis of the handpiece or the electrode shaft.

The constructions of the invention will provide the same important benefits not only for MIS of herniated disks but also for other MIS arthroscopic procedures where controlled electrode position and/or controlled heat generation is of importance as described in the prior applications, as well as for general electrosurgical procedures where the volumetric reduction of tissue or ablation of tissue is desirable.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals designating the same or similar elements.

BRIEF DESCRIPTION OF THE DRAWINGS

In the drawings:

FIG. 1 is a schematic view of a bipolar electrode according to the invention mounted in a handle or handpiece;

FIG. 2 is a perspective view of one form of bipolar electrode according to the invention;

FIG. 3 is a side view of the electrode of FIG. 2;

DETAILED DESCRIPTION OF PREFERRED EMBODIMENTS

Figure 4:
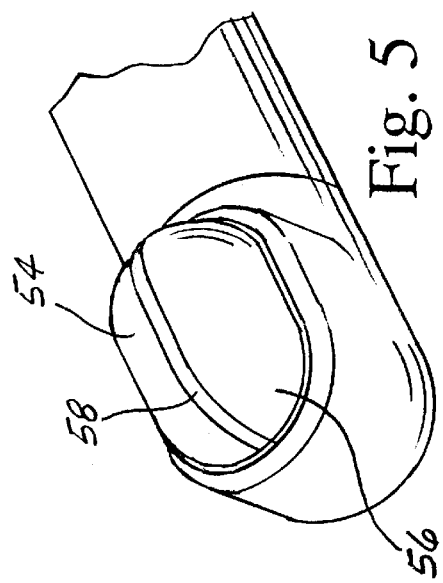
FIG. 4 illustrates one way of assembling the electrode of FIG. 2.

The reader is directed to the referenced prior applications for a more detailed description of the prior applications which will assist in understanding the improvements offered by the present application.

In the present application, FIG. 1 is a schematic view of one form of electrosurgical instrument 10 in accordance with the invention. It comprises a rigid handle 12 with a conventional front end adapted to receive and hold rigidly the shank end (not shown) of an elongated electrode 14 whose working end 16 is shown at the left. The handle 12 is electrically-insulating or if conductive covered with an electrically-insulating coating. Similarly, the electrode elongated shaft 18 is also coated with an electrically-insulating coating, leaving bare the active electrodes 20, 22 at the working end 16. The shaft 18 is long enough to extend through a conventional trocar or channel so that its working end is exposed inside the patient. At the right end of the handle 16 is shown a cable 26 which contains two insulated wires for receiving bipolar electrosurgical currents from a conventional electrosurgical apparatus 28.

FIGS. 1 and 2 illustrate one embodiment of the invention in which the bipolar electrodes 20, 22 are configured as part of an overall hemisphere. Each electrode 20, 22 is substantially one-half of a hemisphere, with their flat sides 30, 32 facing one another and spaced apart by a thin electrically-insulating layer 34. As will be evident from the drawings, the left end 36 of the shaft 18 is molded of an electrically-insulating plastic, such as Nylon (see FIG. 4) to provide a face 38 facing at a 90° angle to the longitudinal axis 40 of the shaft 18. Interior channels 42 in the molded end 36 terminate in openings 44 at the face 38. Located between the holes is a molded insulator 46 with molded pins 48 extending laterally from opposite sides over the openings 44. The bipolar wires 50, shown in FIG. 2, extend respectively, through the channels 42 to the openings 44 where they can be soldered, welded or otherwise electrically connected each to one of a pair of quarter-spherically shaped metal members that constitute the active bipolar electrodes 20, 22. One convenient way of mounting the quarter-spherically shaped metal members is to provide holes in their flat sides 30, 32 which align with the pins 48 on the separator 34, and they can be press fitted or otherwise secured, as by adhesive, to the pins. As will be observed, the two quarter-spherically shaped metal members together with the rounded insulator 34 have their outer surfaces extending in a spherical plane and form almost a complete hemispherical body projecting out of its holder 36 with the electrodes 20, 22 bare and exposed to apply electrosurgical currents to tissue when contacting same. The two wires 50 are not only insulated from each other so that bipolar electrosurgical voltages can be applied between them, but they are also insulated from the electrode holder 36.

In this description, by "axial" is meant parallel to the long axis of the electrode 40 (horizontal in FIGS. 1 and 3). By "lateral" is meant transverse to the long axis 40 of the electrode (vertical in FIGS. 1 and 2). "Lateral" is intended to include 90° for the embodiments of FIGS. 1–5, as well as 45° for the embodiments of FIGS. 6–9. The two insulated wires 50 terminate at the right end of the handle 12 in a connector (not shown) having prongs which can be plugged into the standard bipolar socket or cable which connects the assembly to electrosurgical apparatus 28.

Once the surgeon has positioned the working end 16 of the instrument with respect to the tissue to be operated on, he or she then activates the electrosurgical apparatus 28 causing a discharge of bipolar currents between the bare electrodes 20, 22 capable of causing excision of or ablation of or shrinkage of tissue or cauterization of a blood vessel in the usual way. Other usable mechanical or electrical structures following the teachings of the prior applications will be appreciated by those skilled in this art. As with the embodiments of the prior application, the insulating tube coating on the shaft 18 will prevent accidental touching of patient tissue by the electrode sides, so that the bipolar discharge is locallized to the spacing between the bare ends 20, 22. The operation can take place in a dry or wet field. The surgeon positions the electrodes 20, 22 so as to touch or pass lightly over the tissue to be modulated as needed for the procedure being followed.

For example, a suitable metal for the electrodes is brass or stainless steel. A suitable thickness of the insulator 34 is about 0.02–0.04 inches. The diameter of the hemispherical assembly can vary between about 0.2–0.4 inches. Preferably, the insulator thickness is about 0.025 inches and the radius of curvature of each of the quarter-spherical electrode is about 0.12–0.14 inches. The shaft outside diameter is typically about 0.2–0.4 inches.

Figure 5:
FIG. 5 is a perspective view of another form of bipolar electrode according to the invention.

In the second embodiment of FIG. 5, electrode assembly 54, 56, separated by the thin insulator 58, is more elliptically shaped with its long dimension longer than its transverse dimension. Otherwise, the electrodes are the same.

Figure 6:
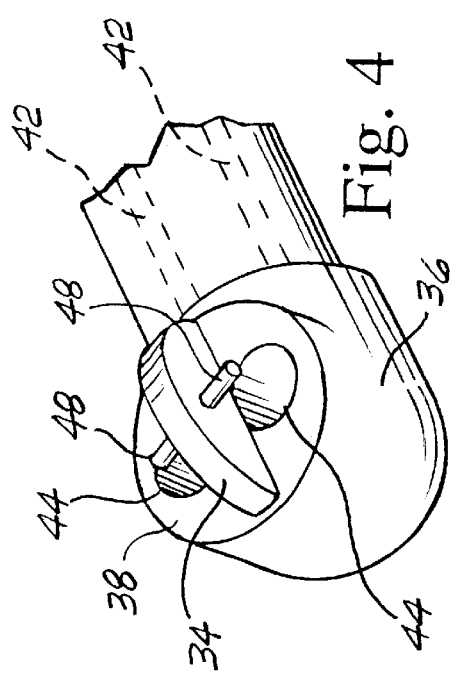
FIGS. 6 and 7 are a side and a perspective view, respectively, of still another form of bipolar electrode according to the invention.
Figure 7:
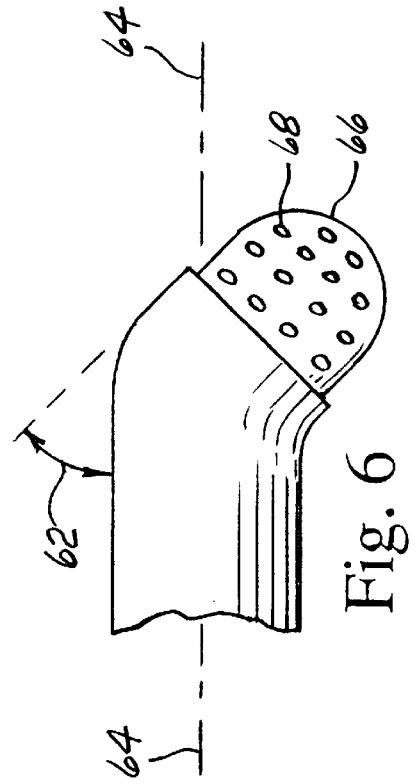

In the third embodiment of FIGS. 6 and 7, there are two differences. First, electrode holder 60 projects at an angle of out 45° (referenced 62) with respect to the longitudinal axis 64 of the holder 60. The electrodes 66 themselves, still forming a hemispherical structure, have holes 68 distributed uniformly about the electrode. As in the other embodiments, the electrodes are spaced apart by a thin insulator 70. The electrosurgical currents tend to concentrate at discontinuities, in this case represented by the edges bordering each hole.

Figure 8:
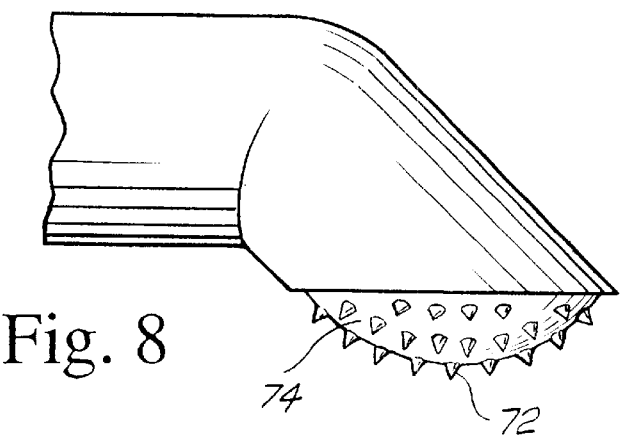
FIGS. 8 and 9 are a side and a perspective view, respectively, of still another form of bipolar electrode according to the invention.
Figure 9:
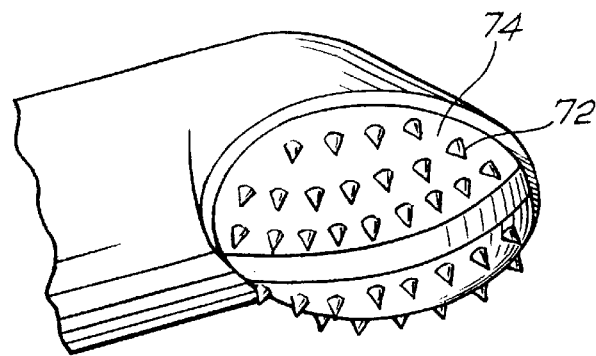

In the fourth embodiment of FIGS. 8 and 9, the electrode 74 is provided with spaced outwardly-projecting points 72 for the purpose of concentrating the electrosurgical currents.

Figure 10:
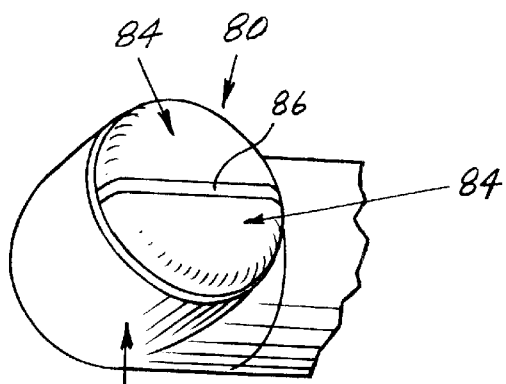
FIG. 10 is a perspective view of another form of bipolar electrode according to the invention.

In the fifth embodiment of FIG. 10, the electrode 80 in a holder 82 has a flattened hemispherical shape with the electrodes 84 spaced apart by a thin insulator 86. While the general shape can still be broadly considered as hemispherical, except for the rounded edges, the top is substantially flat so that when placed adjacent or in contact with the tissue, essentially the whole top surface will be effective. A typical overall diameter is about 0.138 inches, and its height above the holder is about 0.020 inches as an exemplary embodiment.

The electrosurgical apparatus preferably is an ultra high frequency (RF) radiosurgical energy source, which operates in the range of about 3.8–4.0 MHz. Studies have shown that the 3.8–4.0 MHz frequency range is the preferred RF energy to incise and coagulate tissue because tissue thermal necrosis is minimal and, when interfaced with the electrosurgical electrode of the invention, provides excellent cutting and hemostasis especially for throat procedures. An example of suitable electrosurgical apparatus is the Model SURGITRON Dual-Frequency electrosurgical unit manufactured by and available from Ellman International, Inc. of Hewlett, N.Y.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece comprising:
   (a) an elongated first member having a first end and a distal second end,
   (b) first and second electrically-conductive wires positioned in electrically-insulating relationship in the first member with first means connected to the first member at its first end for applying to the first and second wires a bipolar electrosurgical voltage capable of generating electrosurgical currents, each of the first and second wires leading to a bare end configured as a quarter-spherically shaped conductive member projecting laterally out of the first member at its second end,
   (c) the quarter-spherically shaped conductive members being spaced apart by an insulator portion and extending in spaced planes,
   (d) the quarter-spherically shaped conductive members being free of openings at their surfaces,
   (e) wherein electrosurgical currents are generated between the spaced quarter-spherically shaped conductive members when the electrosurgical voltage is applied to the first and second wires.

2. The electrosurgical handpiece as claimed in claim 1, wherein the quarter-spherically shaped conductive members are each constituted of stainless steel or brass.

3. The electrosurgical handpiece as claimed in claim 1, wherein the outer surfaces of the quarter-spherically shaped conductive members and insulator portion form a hemisphere.

4. The electrosurgical handpiece as claimed in claim 3, wherein the second end is rigid.

5. The electrosurgical handpiece as claimed in claim 4, wherein the hemisphere faces at a 90° angle with respect to the longitudinal direction of the first member.

6. The electrosurgical handpiece as claimed in claim 4, wherein the hemisphere faces at a 45° angle with respect to the longitudinal direction of the first member.

7. The electrosurgical handpiece as claimed in claim 1, wherein the hemisphere has spaced outwardly-projecting points.

* * * * *